United States Patent [19]

Cullinan et al.

[11] Patent Number: 5,731,342
[45] Date of Patent: Mar. 24, 1998

[54] BENZOTHIOPHENES, FORMULATIONS CONTAINING SAME, AND METHODS

[75] Inventors: George Joseph Cullinan, Trafalgar; Alan David Palkowitz, Carmel, both of Ind.

[73] Assignee: Eli Lilly and Company, Indianapolis, Ind.

[21] Appl. No.: 787,041

[22] Filed: Jan. 27, 1997

Related U.S. Application Data

[60] Provisional application No. 60/012,044, Feb. 22, 1996.
[51] Int. Cl.$^6$ .................. A61K 31/38; C07D 333/64
[52] U.S. Cl. ........................................ 514/443; 549/52
[58] Field of Search ............................ 549/52; 514/443

[56] References Cited

U.S. PATENT DOCUMENTS 4,380,635  4/1983  Peters et al. ........................ 546/202
4,418,068  11/1983  Jones ................................... 424/267

FOREIGN PATENT DOCUMENTS

584952A1  3/1994  European Pat. Off. .

OTHER PUBLICATIONS

Bates et al., Biochemical Pharmacology, 31(17), pp. 2823–2827 (1982).

Goodman and Gilman's "The Pharmacological Basis of Therapeutics", 6th Ed., MacMillan Publishing Co., NYC, Chapter 1, 1980.

*Primary Examiner*—Mukund J. Shah
*Assistant Examiner*—Michael Bucknum
*Attorney, Agent, or Firm*—James J. Sales; David E. Boone

[57] ABSTRACT

This invention provides novel benzothiophene compounds.

15 Claims, No Drawings

BENZOTHIOPHENES, FORMULATIONS CONTAINING SAME, AND METHODS

This application claims the benefit of U.S. Provisional Application 60/012,044, filed Feb. 22, 1996.

FIELD OF THE INVENTION

This invention relates to the fields of pharmaceutical and organic chemistry and provides benzothiophene compounds, which are useful for the treatment of the various medical indications associated with post-menopausal syndrome and breast cancer treatment and prevention. The invention further relates to pharmaceutical compositions.

BACKGROUND OF THE INVENTION

Osteoporosis describes a group of diseases which arise from diverse etiologies, but which are characterized by the net loss of bone mass per unit volume. The consequence of this loss of bone mass and resulting bone fracture is the failure of the skeleton to provide adequate structural support for the body. One of the most common types of osteoporosis is that associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among post-menopausal women.

There are an estimated 25 million women in the United States alone who are afflicted with this disease. The results of osteoporosis are personally harmful and also account for a large economic loss due its chronicity and the need for extensive and long term support (hospitalization and nursing home care) from the disease sequelae. This is especially true in more elderly patients. Additionally, although osteoporosis is not generally thought of as a life threatening condition, a 20% to 30% mortality rate is related with hip fractures in elderly women. A large percentage of this mortality rate can be directly associated with post-menopausal osteoporosis.

The most vulnerable tissue in the bone to the effects of post-menopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which inter-connect with each other, as well as the more solid and dense cortical tissue which makes up the outer surface and central shaft of the bone. This inter-connected network of trabeculae gives lateral support to the outer cortical structure and is critical to the bio-mechanical strength of the overall structure. In post-menopausal osteoporosis, it is, primarily, the net resorption and loss of the trabeculae which leads to the failure and fracture of bone. In light of the loss of the trabeculae in post-menopausal women, it is not surprising that the most common fractures are those associated with bones which are highly dependent on trabecular support, e.g., the vertebrae, the neck of the weight bearing bones such as the femur and the fore-arm. Indeed, hip fracture, collies fractures, and vertebral crush fractures are hall-marks of post-menopausal osteoporosis.

At this time, the only two generally accepted methods for treatment of post-menopausal osteoporosis are estrogen replacement therapy and bis-phosphonate administration. Although therapy is generally successful, patient compliance with estrogen therapy is low primarily because estrogen treatment frequently produces undesirable side effects. Bis-phosphonate therapy is successful in treating osteoporosis with few serious side-effects; however, it has no effect on the other symptoms related to menopause.

Throughout premenopausal time, most women have less incidence of cardiovascular disease than age-matched men. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can upregulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that post-menopausal women having estrogen replacement therapy have a return of serum lipid levels to concentrations to those of the premenopausal state. Thus, estrogen would appear to be a reasonable treatment for this condition. However, the side-effects of estrogen replacement therapy are not acceptable to many women, thus limiting the use of this therapy. An ideal therapy for this condition would be an agent which would regulate the serum lipid level as does estrogen, but would be devoid of the side-effects and risks associated with estrogen therapy.

Estrogen dependent cancers, especially breast carcinoma, are a major medical problem in women, particularly between the ages of thirty-five to sixty-five. It is estimated most women have a one in ten chance of developing breast cancer in their lifetime. Breast carcinoma is a major cause of mortality in women, as well as a cause of disability, psychological trauma, and economic loss. A large percentage of women contracting this disease eventually die from the effects of it, either directly or indirectly from complications, e.g., metastasis, loss of general health, or collateral effects from therapeutic interventions, such as surgery, radiation, or chemotherapy.

A great deal of benefit has been achieved with the use of hormonally-based therapeutic interventions. The most widely used therapy is the use of tamoxifen. The five-year survival rate for women with breast carcinoma has been dramatically improved with this therapy; however, the longer-term survival (ten-year+) rate has not improved to the same extent. Thus, even with the best combinations of treatment modalities, e.g., surgery, radiation, and/or chemotherapy, the long-term prognosis for patients is poor, especially if metastatic disease is present. Clearly, there is a great need for improved therapies and perhaps more importantly a need for the prevention of the disease in the first instance.

In response to the clear need for new pharmaceutical agents which are capable of alleviating the symptoms of, inter alia, post-menopausal syndrome and the treatment of estrogen dependent cancers, the present invention provides benzothiophene compounds, pharmaceutical compositions thereof, and methods of using such compounds for inhibiting bone loss/osteoporosis, in lowering serum cholesterol levels, and for inhibiting estrogen-dependent cancers.

It is well known in the organic chemistry art that the oxidation of a nitrogen in a compound leads to a reduction of its basicity and an increase in its polarity, i.e., these compounds become more neutral and generally more water soluble. In vivo, it is common that many amine-containing drugs are oxidized to their N-oxides as a part of their metabolism and excretion, as it is a common mechanism for living organisms to eliminate a basic compound. Often the oxidation of the nitrogen leads to compounds which are pharmacologically less active or inactive compared to their parent bases; however, this is unpredictable and must be examined on a case by case basis (see: Goodman and Gilman's "The Pharmacological Basis of Therapeutics", 6th Ed., Macmillan Publishing Co., NYC, Chap. 1, 1980). For example, N-oxidation of the anti-cancer compounds the Vinca alkaloids, leads to biological inactivity (see: Barnett, C. J., et al., *J. Med. Chem.*, 21(1), p. 88–96, 1978).

SUMMARY OF THE INVENTION

This invention provides compounds of formula I

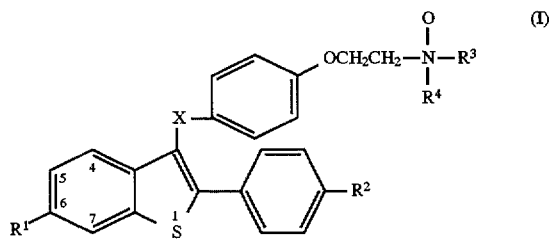

wherein $R^1$ is hydrogen, hydroxy, $C_1$–$C_4$ alkoxy,

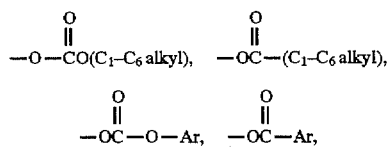

wherein

Ar is optionally substituted phenyl, or —$OSO_2(C_4$–$C_6$ straight chain alkyl);

$R^2$ is $R^1$, Cl or F;

$R^3$ and $R^4$ are, independently, $C_1$–$C_4$ alkyl or combine to form a $C_4$–$C_6$ polymethylene or, together with the nitrogen to which they are attached form morpholine, and X is —$CH_2$—, —$CHOH_2$—, —O—, or

or a pharmaceutically acceptable salt or solvate thereof.

The present invention further relates to pharmaceutical compositions containing a compound of formula I, alone or in combination with other active ingredients.

DETAILED DESCRIPTION OF THE INVENTION

The current invention is related to the discovery that a select group of 2-aryl-3-aroyl (3-arylmethyl, or 3-phenoxy) benzo[b]thiophene amine N-oxides, i.e., the compounds of formula I, are useful for the treatment or prevention of osteoporosis, hyperlipidemia, and estrogen dependent cancers, especially breast cancer.

In the above formula, the term "$C_1$–$C_6$ alkyl" represents a straight or branched alkyl chain having from 1 to 6 carbon atoms. Typical $C_1$–$C_6$ alkyl groups include methyl, ethyl, n-propyl, and n-butyl. The term "$C_1$–$C_4$ alkoxy" represents groups such as methoxy, ethoxy, n-propoxy, and n-butoxy.

Optionally substituted phenyl includes phenyl and phenyl substituted once or twice with $C_1$–$C_6$ alkyl, $C_1$–$C_4$ alkoxy, hydroxy, nitro, chloro, fluoro, or tri(chloro or fluoro)methyl.

When $R^3$ and $R^4$ form a $C_4$–$C_6$ polymethylene, such includes tetramethylene, pentamethylene and hexamethylene. With the nitrogen to which they are attached then, $R^3$ and $R^4$ form for example, pyrrolidino, piperidino, and hexamethyleneimino.

The term "solvate" represents an aggregate that comprises one or more molecules of the solute, such as a formula I compound, with a molecule of solvent.

The term inhibit is defined to include its generally accepted meaning which includes prohibiting preventing, restraining, alleviating, ameliorating, slowing, stopping or reversing progression, or severity, or such action on a resultant symptom. As such, the present invention includes both medical therapeutic and/or prophylactic administration, as appropriate.

Preferred compounds of the current invention include:

[2-(4-hydroxyphenyl)-6-hydroxybenzo[b]thien-3-yl][4-[2-(1-piperidinyl)ethoxy]phenyl]methanone N-oxide,

[2-(4-hydroxyphenyl)-6-hydroxybenzo[b]thien-3-yl][4-[2-(1-piperidinyl)ethoxy]phenyl]methanone N-oxide hydrochloride

[2-(4-hydroxyphenyl)-6-hydroxybenzo[b]thien-3-yl][4-[2-(1-piperidinyl)ethoxy]phenyl]methane N-oxide

[6-hydroxy-3-[4-[2-(1-piperidinyl)ethoxy]phenoxy]-2-(4-methoxyphenyl)]benzo[b]thiophene-N-oxide

[6-hydroxy-3-[4-[2-(1-piperidinyl)ethoxy]phenoxy]-2-(4-hydroxyphenyl)]benzo[b]thiophene-N-oxide The compounds of the current invention (formula I) are prepared by the selective oxidation of the basic nitrogen of the compounds of formula II, below.

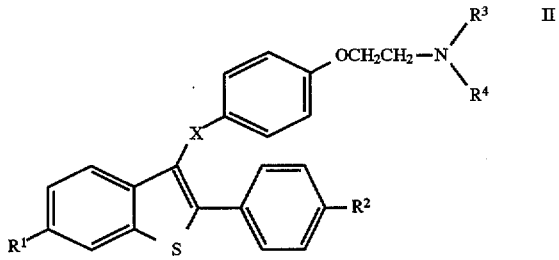

The compounds of formula II can be made according to established procedures. Compounds of formula II, where X is —CO—, can be prepared by the proceedures detailed in U.S. Pat. Nos. 4,133,814, 4,418,068, and 4,380,635, all of which are incorporated by reference herein.

In general, the process starts with a benzo[b]thiophene having a 6-hydroxyl group and a 2-(4-hydroxyphenyl) group. The starting compound is protected, acylated, and deprotected to form the formula II compounds. Examples of the preparation of such compounds are provided in the U.S. patents discussed above.

The formula II compounds which are carboxylic esters or sulfonates may be prepared by methods described in U.S. Pat. No. 5,393,763, U.S. Pat. Nos. 5,482,949 and 5,482,949, each of which is incorporatedby reference herein. Modifications to the above methods may be necessary to accommodate reactive functionalities of particular substituents. Such modifications would be both apparent to, and readily ascertained by, those skilled in the art of organic chemistry.

Compounds of formula II, where X is —$CH_2$— or —CHOH—, may be prepared by the proceedures described in U.S. Pat. No. 5,484,798, which is incorporated by reference herein. Briefly, reduction of the carbonyl to the carbinol, and further to the methylene, may be accomplished step-wise or from the carbonyl to the methylene in a single step.

The carbonyl compounds of formula II can be reduced to the carbinol with $LiAlH_4$, $NaBH_4$, or the like in appropriate solvents such chlorocarbons, THF, ether, etc. at temperatures of 0°–30° C. The carbinol may be reduced to the methylene with alkylsilanes and trifluoroacetic acid, e.g., triethylsilane, in appropriate solvents such as, methylene chloride, or THF at ambient temperatures. Alternatively, the carbonyl compound may be reduced directly to the methylene by using $LiAlH_4$ in a high boiling solvent such as propylbenzene at reflux temperatures.

Compounds of formula II, where X is —O—, may be prepared by the proceedures described in U.S. Pat. No. 5,488,058, which is incorporated by refence, herein. Briefly, a 2-aryl benzo[b]thiophene is brominated on the 3-position. This bromide is displaced by a phenoxide containing the basic side-chain under Ullman reaction conditions.

Oxidation of the nitrogen on the 3-aroyl, 3-phenoxy, or 3-arylmethyl side-chain of the compounds of formula II is accomplished by the use of dilute aqueous solutions of $H_2O_2$ with a co-solvent such as methanol or ethanol or halogenated hydrocarbons. Reaction conditions for this reaction may range from ambient temperature to 100° C. and in duration from 1 to 72 hours. It should be noted that care must be taken in selecting the oxidizing agent and that many commonly used agents, e.g., $CrO_3$, $KMnO_4$, and the like, capable of oxidizing the nitrogen can not be used, since they would also oxidize the sulfur of the benzo[b]thiophene. Thus, a milder agent such as $H_2O_2$ is preferred. Examples of the preparation of the compounds of formula I using this procedure are listed below.

Below are examples of the preparation of the compounds of formula I. They are presented for the purpose of illustration and it in no way is considered to be limiting the scope of this invention.

EXAMPLE 1

[2-(4-Hydroxyphenyl)-6-hydroxybenzo[b]thien-3-yl][4-[2-(1-piperidinyl)ethoxy]phenyl]methanone N-oxide Two grams (4.23 mmol) of [2-(4-Hydroxyphenyl)-6-hydroxybenzo[b]thien-3-yl][4-[2-(1-piperdinyl)ethoxy]phenyl]methanone was dissolved in 150 mL of refluxing EtOH and 15 mL of 30% aqueous $H_2O_2$ was added. The reaction mixture was refluxed for eighteen hours, then checked for completeness by tlc. An additional 15 mL of 30% $H_2O_2$ was added and the reaction was allowed to continue for an additional eighteen hours at reflux temperature. The reaction was allowed to cool and the volatile solvents were removed by evaporation in vacuo. The crude material was re dissolved in $CHCl_3$ and partitioned with water. The $CHCl_3$ layer was dried by filtration through anhydrous $Na_2SO_4$ and evaporated to dryness. This yielded 1590 mg of the title compound as a light yellow amorphous powder.

PMR: ($CDCl_3$-DMSO-$d_6$) 7.70 δ(d, J=6 Hz, 2H), 7.43 (d, J=4 Hz, 1H), 7.27 (d, J=1 Hz, 1H), 7.15 (D, J=5 Hz, 2H), 6.87 (dd, $J_1$=4 Hz, $J_2$=1 Hz, 1H), 6.77 (d, J=5 Hz, 2H), 6.65 (d, J=6 Hz, 2H), 4.54 (t, J=2 Hz, 2H), 3.71 (t, J=2 Hz, 2H), 3.38 (m, 4H), 2.16 (m, 2H), 1.72 (m, 3H), 1.48 (m, 1H) MS: m/e=490 (M+) FD pKa: 6.28 Apparent Molecular Weight (amw)=487 (66% DMF) $R_f$: 0.05 silica gel $CHCl_3$—MeOH (19:1) (v/v) EA: Calc: C, 66.3; H, 5.73; N, 2.76 Found: C, 66.46; H, 5.62; N, 2.76 $C_{28}H_{27}NO_5S$—$H_2O$

EXAMPLE 2

[2-(4—Methoxyphenyl)-6-methoxybenzo[b]thien-3-yl][4-[2-(1-piperidinyl)ethoxy]phenyl]methanone N-oxide 1190 mg (2.38 mmol) [2-(4—Methoxyphenyl)-6-methoxybenzo[b]thien-3yl][4-[2-(1-piperidinyl)ethoxy]phenyl]methanone was dissolved in 100 mL of methanol and 30 mL of 30% $H_2O_2$ was added. The reaction mixture turned cloudy, but cleared after several hours. The reaction was allowed to proceed for 72 hours at ambient temperature. The reaction mixture was evaporated to dryness and extracted into 100 mL of EtOAc. The EtOAc solution was washed with dilute, aqueous Nalco and dried by filtration through anhydrous $Na_2SO_4$. Hexane was added and the solution allowed to crystallize at −20° C. A tan solid was filter and dried, yielding 720 mg of the title compound.

PMR: consistent with the proposed structure MS: m/e= 501 (M-16 FD pKa: 6.39 amw=517 (66% DMF) $R_f$: 0.07 silica gel $CHCl_3$—MeOH (19:1) (v/v)

EXAMPLE 3

[2-(4-Hydroxyphenyl)-6-hydroxybenzo[b]thien-3-yl][4-[2-(N,N-diethyl)ethoxy]phenyl]methanone N-oxide 2000 mg (4.33 mmol) of [2-(4-Hydroxyphenyl)-6-hydroxybenzo[b]thien-3-yl][4-[2-(N,N-diethyl)ethoxy]phenyl]methanone was dissolved in 60 mL of methanol and 10 mL of 30% $H_2O_2$ was added. The reaction was allowed to proceed for eighteen hours at ambient temperature. The reaction mixture was evaporated to dryness and re-dissolved in 100 mL of EtOAc. The EtOAc solution was washed with water and dried with $Na_2SO_4$ and evaporated to dryness. This resulted in obtaining 1150 mg of the title compound as tan amorphous powder.

PMR: consistent with the proposed structure MS: m/e= 478 (M+) and 462 (M-16) FD pKa: 6.15 amw=498 (66% DMF) $R_f$: 0.14 silica gel $CHCl_3$—MeOH (19:1) (v/v)

EXAMPLE 4

[2-(4-Hydroxyphenyl)-6-hydroxybenzo[b]thien-3-yl][4-[2-(1-morpholino)ethoxy]phenyl]methanone N-oxide 1100 mg (2.23 mmol) of [2-(4-Hydroxyphenyl)-6-hydroxybenzo[b]thien-3-yl][4-[2-(1-morpholino)ethoxy]phenyl]methanone was dissolved in 50 mL of methanol and 30 mL of 10% $H_2O_2$ was added. The reaction was allowed to proceed for eighteen hours at ambient temperature. The reaction was checked by tlc and an additional 10 mL of 30% $H_2O_2$ was added. The reaction was continued for an additional eighteen hours. The reaction mixture was evaporated to dryness and re dissolved in 100 mL of EtOAc. The EtOAc solution was washed with dilute, aqueous NaCl and dried with $Na_2SO_4$ and evaporated to dryness. This yielded 460 mg of the title compound as a tan amorphous powder.

PMR: Consistent with the proposed structure MS: m/e= 492 (M+) and 475 (M-16) FD $R_f$: 0.04 silica gel $CHCl_3$—MeOH (19:1) (v/v)

EXAMPLE 5

[2-(4-n-Butylsulfonoylphenyl)-6-n-butylsulfonoylbenzo[b]thien-3-yl][4-[2-(1-piperidinyl)ethoxy]phenyl]methanone N-oxide 1250 mg (1.27 mmol) of [2-(4-n-butylsulfonoylphenyl)-6-n-butylsulfonoylbenzo[b]thien-3-yl][4-[2-(1-piperidinyl)ethoxy]phenyl]methanone was dissolved in 125 mL of MeOH and 25 mL of EtOH and 30 mL of 30% $H_2O_2$ was added. The reaction was allowed to proceed for eighteen hours at ambient temperature. The reaction mixture was evaporated to dryness and re-dissolved in 100 mL of EtOAc. The EtOAc solution was washed with water and dried with $Na_2SO_4$ and evaporated to dryness. This resulted in 390 mg of the title compound as a tan amorphous powder.

PMR: consistent with the proposed structure MS: m/e= 730 (M+) and 714 (M-16) FD $R_f$: 0.16 silica gel $CHCl_3$—MeOH (19:1) (v/v)

EXAMPLE 6

[2-(4-Hydroxyphenyl)-6-hydroxybenzo[b]thien-3-yl][4-[2-(1-piperidinyl)ethoxy]phenyl]methanol N-oxide A solution was prepared of 10 mL of 10% $H_2O_2$ and 100 mL of MeOH. To this solution was added 476 mg (1 mmol) of [2-(4-Hydroxyphenyl)-6-hydroxybenzo[b]thien-3-yl][4-[2-(1-piperidinyl)ethoxy]phenyl]methanol. The reaction was allowed to proceed for twenty hours at ambient temperature. The reaction mixture was evaporated to dryness and triturated several times with toluene. The product was dried in vacuo. This yielded 230 mg of the title compound as a tan amorphous powder.

PMR: Consistent with the proposed structure. MS: m/e= 492 (M+) and 476 (M-16) FD p$K_a$=6.41 EA: Calc. for $C_{28}H_{29}NO_5S\cdot2H_2O$: C, 63.7; H, 5.87; N, 2.65 Found: C, 63.13; H, 5.81; N, 2.43.

EXAMPLE 7

[2-(4-Hydroxyphenyl)-6-hydroxybenzo[b]thien-3-yl][4-[2-(1-piperidinyl)ethoxy]phenyl]methane N-oxide A solution was prepared of 20 mL of 10% $H_2O_2$ and 100 mL of MeOH, to which was added 1500 mg (3.27 mmol) of [2-(4-hydroxyphenyl)-6-hydroxybenzo[b]thien-3-yl][4-[2-(1-piperidinyl)ethoxy]phenyl]methane. The reaction mixture was stirred at ambient temperature for twenty hours. The reaction mixture evaporated to dryness in vacuo and triturated several times with toluene. The reaction product was dried in vacuo at ambient temperature for several days. This yielded 1090 mg of the title compound as a tan amorphous powder.

PMR: (CDCl$_3$) 7.42 δ (d, J=4 Hz, 4H), 7.40 (d, J=4 Hz, 1H), 7.38 (d, J=1 Hz, 1H), 7.18 (d, J=4 Hz, 2H), 7.00 (d, J=4 Hz, 2H), 6.98(m,1H), 6.92 (d, J=4 Hz, 2H), 4.69 (t, J=2 Hz, 2H), 4.27(s, 2H), 3.78(t, J=2 Hz, 2H), 2.35–2.60(m, 4H), 2.38(m, 2H), 1.83 (m,2H), 1.60 (m, 1H) MS: m/e=459 (m-16) FD p$K_a$: 6.49 amw=461 EA: Calc. for $C_{28}H_{29}NO_4S$: C, 70.71; H, 6.15; N, 2.95 Found; C, 70.12; H, 6.11; N, 3.09.

EXAMPLE 9

[6-Hydroxy-3-[4-[2-(1-piperidinyl)ethoxy]phenoxy]-2-(4-methoxyphenyl)]benzo[b]thiophene-N-oxide

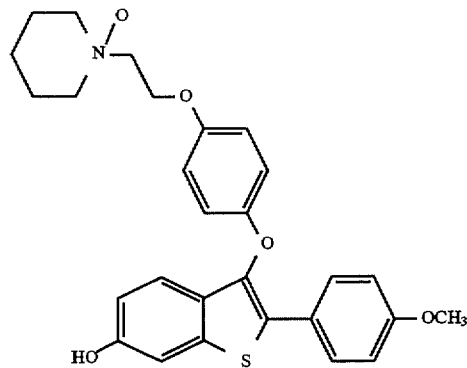

To a solution of [6-hydroxy-3-[4-[2-(1-piperidinyl)ethoxy]phenoxy]-2-(4-methoxyphenyl)]benzo[b]thiophene (50 mg, 0.10 mmol) in 3 mL of 1:1 CH$_3$OH/CHCl$_3$ was added $H_2O_2$ (0.5 mL of a 30% solution). The resulting mixture was gently warmed on a steam bath until TLC analysis showed that the reaction was complete (1–2 h). The solvent was then removed in vacuo to give a yellow solid that was triturated from EtOH/Et$_2$O. Filtration provided 46 mg (92%) of [6-hydroxy-3-[4-[2-(1-piperidinyl)ethoxy] phenoxy]-2-(4-methoxyphenyl)]benzo[b]thiophene-N-oxide as a yellow solid.

mp 120°–125° C. $^1$H NMR (DMSO-d$_6$) δ 10.30 (bs, 1H), 7.53 (d, J=8.8 Hz, 2H), 7.15 (d, J=2.0 Hz, 1H), 7.00 (d, J=8.7 Hz, 1H), 6.93 (d, J=8.8 Hz, 2H), 6.79 (s, 4H), 6.72 (dd, J=8.7, 2.0 Hz, 1H), 4.38 (m, 2H), 3.71 (s, 3H), 3.50–3.03 (m, 6H), 2.02 (m, 2H), 1.51–1.13 (m, 3H), 1.05 (m, 1H). FD mass spec: 492, 475, 390, 364. Anal. Calcd. for $C_{28}H_{29}NO_5S\cdot0.45H_2O$: C, 67.30; H, 6.03; N, 2.80. Found: C, 67.31; H, 5.96; N, 2.57.

EXAMPLE 10

[6-Hydroxy-3-[4-[2-(1-piperidinyl)ethoxy]phenoxy]-2-(4-hydroxyphenyl)]benzo[b]thiophene-N-oxide

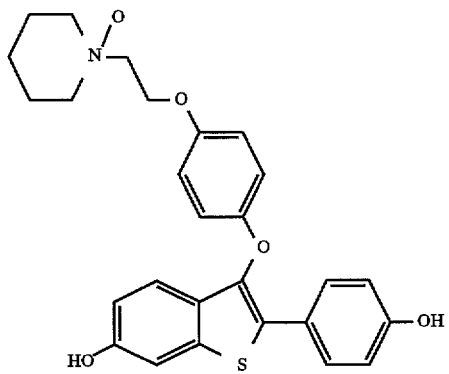

Prepared in a similar manner as described in Example 10 was the above-titled compound.

mp 125°–130° C. $^1$H NMR (DMSO-d$_6$) δ 7.39 (d, J=8.6 Hz, 2H), 7.15 (d, J=2.1 Hz, 1H), 6.99 (d, J=8.7 Hz, 1H), 6.77 (s, 4H), 6.73 (dd, J=8.7 Hz, 2.1 Hz, 2H), 6.71 (d, J=8.6 Hz, 2H), 4.37 (m, 2H), 3.52 (m, 2H), 3.38–3.03 (m, 4H), 2.04 (m, 2H), 1.53–1.49 (m, 3H), 1.31 (m, 1H). FD mass spec: 477, 460. Anal. Calcd. for $C_{27}H_{27}NO_5S\cdot0.5H_2O$: C, 66.65; H, 5.80; N, 2.88. Found: C, 66.66; H, 5.98; N, 2.89.

The following examples illustrate the methods of use for the compounds of formula I in experimental models or clinical studies.

TEST PROCEDURE

General Preparation Procedure

In the examples illustrating the methods, a postmenopausal model was used in which effects of different treatments upon circulating lipids were determined.

Seventy-five day old female Sprague Dawley rats (weight range of 200 to 225 g) are obtained from Charles River Laboratories (Portage, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage and have ad libitum access to food (calcium content approximately 0.5%) and water for one week. Room temperature is maintained at 22.2°±1.7° C. with a minimum relative humidity of 40%. The photoperiod in the room is 12 hours light and 12 hours dark.

Dosing Regimen Tissue Collection

After a one week acclimation period (therefore, two weeks post-OVX) daily dosing with test compound is initiated. 17α-ethynyl estradiol or the test compound is given orally, unless otherwise stated, as a suspension in 1% carboxymethylcellulose or dissolved in 20% cyclodextrin. Animals were dosed daily for 4 days. Following the dosing regimen, animals are weighed and anesthetized with a ketamine: Xylazine (2:1, V:V) mixture and a blood sample is collected by cardiac puncture. The animals are then sacrificed by asphyxiation with $CO_2$, the uterus is removed through a midline incision, and a wet uterine weight is determined.

Cholesterol Analysis

Blood samples are allowed to clot at room temperature for 2 hours, and serum is obtained following centrifugation for 10 minutes at 3000 rpm. Serum cholesterol is determined using a Boehringer Mannheim Diagnostics high performance cholesterol assay. Briefly the cholesterol is oxidized to cholest-4-en-3-one and hydrogen peroxide. The hydrogen peroxide is then reacted with phenol and 4-aminophenazone in the presence of peroxidase to produce a p-quinone imine dye, which is read spectrophotemetrically at 500 nm. Cholesterol concentration is then calculated against a standard curve. The entire assay is automated using a Biomek Automated Workstation.

Uterine Eosinophil Peroxidase (EPO) Assay

Uteri are kept at 4° C. until time of enzymatic analysis. The uteri are then homogenized in 50 volumes of 50 mM Tris buffer (pH—8.0) containing 0.005% Triton X-100. Upon addition of 0.01% hydrogen peroxide and 10 mM O-phenylenediamine (final concentrations) in Tris buffer, increase in absorbance is monitored for one minute at 450 nm. The presence of eosonophils in the uterus is an indication of estrogenic activity of a compound. The maximal velocity of a 15 second interval is determined over the initial, linear portion of the reaction curve.

Source of Compound

17α-ethynyl estradiol was obtained from Sigma Chemical Co., St. Louis, Mo.

Hyperlipidemia

Data presented in Table 1 show comparative results among ovariectomized rats, rats treated with 17-a-ethynyl estradiol ($EE_2$), and rats treated with certain compounds of this invention. Although $EE_2$ caused a decrease in serum cholesterol when orally administered at 0.1 mg/kg/day, it also exerted a simulatory effect on the uterus so that $EE_2$ uterine weight was substantially greater than the uterine weight of the ovariectomized animals. This uterine response to an estrogen is well recognized in the art.

The compounds of the present invention reduced serum cholesterol compared to the ovariectomized animals.

As expressed in the data below, estrogenicity also was assessed by evaluating the response of eosinophil infiltration into the uterus. The compounds of this invention did not cause a large increase in the number of eosinophils observed in the stromal layer of the ovariectomized, rat uteri. $EE_2$ caused a substantial and expected increase in eosinophil infiltration.

The data presented in Table 1 reflect the response of five or six rats per treatment group.

TABLE 1

| Compound No. (Example No.) | Dose mg/kg[a] | Uterine Weight % Inc[b] | Uterine Eosinophil (Vmax)[c] | Serum Cholest. % Dec.[d] |
|---|---|---|---|---|
| $EE_2$[e] | 0.1 | 207.5* | 205.8* | 87.3* |
| 1 | 0.1 | 31.2* | 4.4 | 44.9* |
|  | 1.0 | 29.6* | 4.6 | 68.7* |
|  | 10.0 | 8.3 | 2.5 | 70.3* |
| 2 | 1.0 | 49.2* | 11.2 | 65.7* |

TABLE 1-continued

| Compound No. (Example No.) | Dose mg/kg[a] | Uterine Weight % Inc[b] | Uterine Eosinophil (Vmax)[c] | Serum Cholest. % Dec.[d] |
|---|---|---|---|---|
| 3 | 1.0 | 77.5* | 21.7* | 64.2* |
| 4 | 1.0 | 62.5* | 4.1 | 56.2* |
| 5 | 1.0 | 44.4* | 4.7 | 74.9* |

[a]17-a-Ethylyl estradiol
[b]Uterine Weight % increase versus the ovarierectomized controls
[c]Eosinphil peroxidase Vmaxium
[d]Serum cholesterol decrease versus ovariectomized controls
*p<.05

Osteoporosis Test Procedure

Following the General Preparation Procedure, infra, the rats are treated daily for 35 days (6 rats per treatment group) and sacrificed by carbon dioxide asphyxiation on the 36th day. The 35 day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized x-rays generated and analyzed by an image analysis program (NIH image) at the distal metaphysis. The proximal aspect of the tibiae from these animals are also scanned by quantitative computed tomography.

In accordance with the above procedures, compounds of the present invention and ethynyl estradiol ($EE_2$) in 20% hydroxypropyl β-cyclodextrin are orally administered to test animals.

In summary, ovariectomy of the test animals causes a significant reduction in femur density compared to intact, vehicle treated controls. Orally administered ethynyl estradiol ($EE_2$) prevented this loss, but the risk of uterine stimulation with this treatment is ever-present.

The compounds of the present invention prevent bone loss in a general, dose-dependent manner.

MCF-7 Proliferation Assay

MCF-7 breast adenocarcinoma cells (ATCC HTB 22) are maintained in MEM (minimal essential medium, phenol red-free, Sigma, St. Louis, Mo.) supplemented with 10% fetal bovine serum (FBS) (V/V), L-glutamine (2 mM), sodium pyruvate (1 mM), HEPES {(N-[2-hydroxyethyl] piperazine-N'-[2-ethanesulfonic acid]10 mM}, non-essential amino acids and bovine insulin (1 ug/mL) (maintenance medium). Ten days prior to assay, MCF-7 cells are switched to maintenance medium supplemented with 10% dextran coated charcoal stripped fetal bovine serum (DCC-FBS) assay medium) in place of 10% FBS to deplete internal stores of steroids. MCF-7 cells are removed from maintenance flasks using cell dissociation medium (Ca++/Mg++ free HBSS (phenol red-free) supplemented with 10 mM HEPES and 2 mM EDTA). Cells are washed twice with assay medium and adjusted to 80,000 cells/mL. Approximately 100 μL (8,000 cells) are added to flat-bottom microculture wells (Costar 3596) and incubated at 37° C. in a 5% $CO_2$ humidified incubator for 48 hours to allow for cell adherence and equilibration after transfer. Serial dilutions of drugs in assay medium and 50 μL transferred to triplicate microcultures followed by 50 μL assay medium for a final volume of 200 μL. After an additional 48 hours at 37° C. in a 5% $CO_2$ humidified incubator, microcultures are pulsed with tritiated thymidine (1 uCi/well) for 4 hours. Cultures are terminated by freezing at −70° C. for 24 hours followed by thawing and harvesting of microcultures using a Skatron Semiautomatic Cell Harvester. Samples are counted by liquid scintillation using a Wallac BetaPlace β counter. For example, in this assay, the compound of Example 1 has an $IC_{50}$ of approximately 1 μM.

DMBA-Induced Mammary Tumor Inhibition

Estrogen-dependent mammary tumors are produced in female Sprague-Dawley rats which are purchased from Harlan Industries, Indianapolis, Ind. At about 55 days of age, the rats receive a single oral feeding of 20 mg of 7,12-dimethylbenz[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

Compounds of Formula I are administered either through intraperitoneal injections in 2% acacia, or orally. Orally administered compounds are either dissolved or suspended in 0.2 mL corn oil. Each treatment, including acacia and corn oil control treatments, is administered once daily to each test animal. Following the initial tumor measurement and selection of test animals, tumors are measured each week by the above-mentioned method. The treatment and measurements of animals continue for 3 to 5 weeks at which time the final areas of the tumors are determined. For each compound and control treatment, the change in the mean tumor area is determined.

Activity in at least one of the above assays illustrates the utility of the compounds of formula I.

The compounds of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene methanol, ethanol, or acetone. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

It is usually preferred to administer a compound of formula I in the form of an acid addition salt, as is customary in the administration of pharmaceuticals bearing a basic group, such as the piperidino ring. It is also advantageous to administer such a compound by the oral route.

As used herein, the term "effective amount" means an amount of a compound of formula I, or optionally, an amount of a compound of formula I combined with an amount of a compound of formula II, which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 0.1 mg to about 1000 mg/day of a compound of the present invention, and more particularly will be from about 20 mg to about 200 mg/day.

The compounds of this invention can be administered by a variety of routes including oral, rectal, transdermal, subcutaneus, intravenous, intramuscular, and intranasal. These compounds preferably are formulated prior to administration, the selection of which will be decided by the attending physician.

The total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

An active ingredient in the formulations, below, means a compound of formula I.

Pharmaceutical formulations of the present invention can be prepared by procedures known in the art using well known and readily available ingredients. For example, the compounds of formula I, with or without another active agent, such as a compound of formula II, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

The following formulation examples only are illustrative and are not intended to limit the scope of the present invention.

FORMULATIONS

Formulation 1

Gelatin Capsules

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:

Formulation 2

Tablets

| Ingredient | Quantity (mg/tablet) |
| --- | --- |
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5–1000 mg of active ingredient are made up as follows:

Formulation 3

Tablets

| Ingredient | Quantity (mg/tablet) |
| --- | --- |
| Active ingredient | 25–1000 |
| Starch | 45 |
| Cellulose, microcrystalline | 35 |

-continued

| Ingredient | Quantity (mg/tablet) |
| --- | --- |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:

Formulation 4

Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 5

Aerosol

| Ingredient | Quantity (% by weight) |
| --- | --- |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

Formulation 6

Suppositories

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7

Intravenous Solution

| Ingredient | Quantity |
| --- | --- |
| Active ingredient | 50 mg |
| Isotonic saline | 1,000 mL |

The solution of the above ingredients is intravenously administered to a patient at a rate of about 1 mL per minute.

Formulation 8

Combination Capsule I

| Ingredient | Quantity (mg/capsule) |
| --- | --- |
| Active ingredient | 50 |
| Premarin | 1 |
| Avicel pH 101 | 50 |
| Starch 1500 | 117.50 |
| Silicon Oil | 2 |
| Tween 80 | 0.50 |
| Cab-O-Sil | 0.25 |

Formulation 9

Combination Capsule II

| Ingredient | Quantity (mg/capsule) |
| --- | --- |
| Active ingredient | 50 |
| Norethylnodrel | 5 |
| Avicel pH 101 | 82.50 |
| Starch 1500 | 90 |
| Silicon Oil | 2 |
| Tween 80 | 0.50 |

Formulation 10

Combination Tablet

| Ingredient | Quantity (mg/capsule) |
| --- | --- |
| Active ingredient | 50 |
| Premarin | 1 |
| Corn Starch NF | 50 |
| Povidone, K29–32 | 6 |
| Avicel pH 101 | 41.50 |

-continued

| Ingredient | Quantity (mg/capsule) |
| --- | --- |
| Avicel pH 102 | 136.50 |
| Crospovidone XL10 | 2.50 |
| Magnesium Stearate | 0.50 |
| Cab-O-Sil | 0.50 |

Formulation 8

Gelatin Capsules

Hard gelatin capsules are prepared using the following:

| Ingredient | Quantity (mg/capsule) |
| --- | --- |
| Compound of Formula I | 0.1–1000 |
| Compound of Formula II | 0.1–1000 |
| Starch NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:

Formulation 9

Tablets

| Ingredient | Quantity (mg/tablet) |
| --- | --- |
| Compound of Formula II | 2.5–1000 |
| Compound of Formula I | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 25–1000 mg of active ingredient are made up as follows:

Formulation 10

Tablets

| Ingredient | Quantity (mg/tablet) |
| --- | --- |
| Compound of Formula II | 24.75–990 |
| Compound of Formula I | 0.25–10 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredients, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Formulation 11

Tablets

| Ingredient | Quantity (mg/tablet) |
|---|---|
| Compound of Formula II | 25–1000 |
| Compound of Formula I | 0.025–1.0 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredients, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Formulation 12

Tablets

| Ingredient | Quantity (mg/tablet) |
|---|---|
| Compound of Formula II | 60 |
| Compound of Formula I | 0.06–0.18 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredients, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

We claim:

1. A compound of formula I (I)

wherein
$R^1$ is hydrogen, hydroxy, $C_1$–$C_4$ alkoxy, $$-O-CO(C_1-C_6\text{alkyl}),\ -OC-(C_1-C_6\text{alkyl}),$$

$$-OC-O-Ar,\ -OC-Ar,$$

wherein Ar is optionally substituted phenyl, or $-SO_2$ ($C_4$–$C_6$ straight chain alkyl);

$R^2$ is $R^1$, Cl or F; and $R^3$ and $R^4$ are, independently, $C_1$–$C_4$ alkyl or combine to form a $C_4$–$C_6$ polymethylene or, together with the nitrogen to which they are attached form morpholine, X is $-CH_2$, $-CHOH-$, $-O-$, or $$-\overset{O}{\underset{\|}{C}}-;$$

or a pharmaceutically acceptable salt or solvate thereof.

2. A compound according to claim 1 wherein said compound is [2-(4-hydroxyphenyl)-6-hydroxybenzo[b]thien-3-yl][4-[2-(1-piperidinyl)ethoxy]phenyl]methanone-N-oxide.

3. A compound according to claim 2 wherein said compound is the hydrochloride salt thereof.

4. A compound according to claim 1 wherein said compound is [6-hydroxy-3-[4-[2-(1-piperidinyl)ethoxy]phenoxy]-2-(4-methoxyphenyl)]benzo[b]thiophene-N-oxide.

5. A compound according to claim 1 wherein said compound is [6-hydroxy-3-[4-[2-(1-piperidinyl)ethoxy]phenoxy]-2-(4-hydroxyphenyl)]benzo[b]thiophene-N-oxide.

6. A compound according to claim 4 wherein said compound is the hydrochloride salt thereof.

7. A method for inhibiting osteoporosis which comprises, administering to patient in need thereof an effective amount of a compound of claim 1.

8. A method for lowering serum cholesterol levels which comprises administering to a patient in need thereof an effective amount of a compound of claim 1.

9. A method for inhibiting estrogen-dependent cancer comprising administering to a patient in need thereof an effective amount of a compound of claim 1.

10. A formulation comprising a compound of formula I of claim 1 and, optionally, pharmaceutically acceptable carriers, diluents, or excipients therefor.

11. A pharmaceutical formulation comprising a compound of formula I of claim 1 and further comprising [2-(4-hydroxyphenyl)-6-hydroxybenzo[b]thien-3-yl][4-[2-(1-piperidinyl)ethoxy]phenyl]methanone hydrochloride and, optionally, pharmaceutically acceptable carriers, diluents, or excipients therefor.

12. A formulation according to claim 11 wherein the formula I compound comprises less than 10% by weight of the total active ingredients.

13. A formulation according to claim 12 wherein the formula I compound comprises less than 1% by weight of the total active ingredients.

14. A formulation according to claim 13 wherein the formula I compound comprises less than 0.3% by weight of the total active ingredients.

15. A formulation according to claim 11 wherein said formula I compound is [2-(4-hydroxyphenyl)-6-hydroxybenzo[b]thien-3-yl][4-[2-(1-piperidinyl)ethoxy]phenyl]methanone-N-oxide.

* * * * *